United States Patent
Hikosaka

(10) Patent No.: US 9,936,927 B2
(45) Date of Patent: Apr. 10, 2018

(54) X-RAY IMAGING APPARATUS AND CONTROL METHOD

(71) Applicant: CANON KABUSHIKI KAISHA, Tokyo (JP)

(72) Inventor: Manami Hikosaka, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 502 days.

(21) Appl. No.: 14/662,392

(22) Filed: Mar. 19, 2015

(65) Prior Publication Data

US 2015/0272526 A1 Oct. 1, 2015

(30) Foreign Application Priority Data

Mar. 31, 2014 (JP) .................... 2014-073734

(51) Int. Cl.
*A61B 6/00* (2006.01)
*A61B 8/00* (2006.01)

(52) U.S. Cl.
CPC .............. *A61B 6/467* (2013.01); *A61B 6/465* (2013.01); *A61B 6/54* (2013.01); *A61B 6/545* (2013.01); *A61B 8/465* (2013.01); *A61B 8/54* (2013.01); *A61B 6/4208* (2013.01)

(58) Field of Classification Search
CPC ......... A61B 6/04; A61B 6/4208; A61B 6/465; A61B 6/467; A61B 6/545; A61B 6/548; A61B 6/563
See application file for complete search history.

(56) References Cited

U.S. PATENT DOCUMENTS

| | | | |
|---|---|---|---|
| 8,077,828 B2 | 12/2011 | Aoyama | |
| 8,649,482 B2 | 2/2014 | Abe | |
| 2004/0254439 A1* | 12/2004 | Fowkes | A61B 8/00 600/407 |
| 2007/0003017 A1* | 1/2007 | Boese | A61B 6/12 378/116 |
| 2012/0051519 A1 | 3/2012 | Abe | 378/98 |
| 2014/0029833 A1 | 1/2014 | Hikosaka | |
| 2014/0064448 A1* | 3/2014 | Ito | A61B 6/542 378/62 |

FOREIGN PATENT DOCUMENTS

| | | |
|---|---|---|
| JP | 2001-275988 | 10/2001 |
| JP | 2003-248723 | 9/2003 |
| JP | 2009207812 A | 9/2009 |
| JP | 2012-050620 | 3/2012 |
| JP | 2012-100797 | 5/2012 |

* cited by examiner

*Primary Examiner* — Glen Kao
(74) *Attorney, Agent, or Firm* — Fitzpatrick Cella Harper and Scinto

(57) ABSTRACT

A control apparatus for an X-ray imaging system obtains examination information including a plurality of imaging techniques and a plurality of imaging conditions corresponding to the plurality of imaging techniques. When the content of a condition item of the imaging condition selected from the plurality of imaging conditions is changed in accordance with an operation input from the operator, the control apparatus applies the change to an imaging condition other than the selected imaging condition of the plurality of imaging conditions.

18 Claims, 12 Drawing Sheets

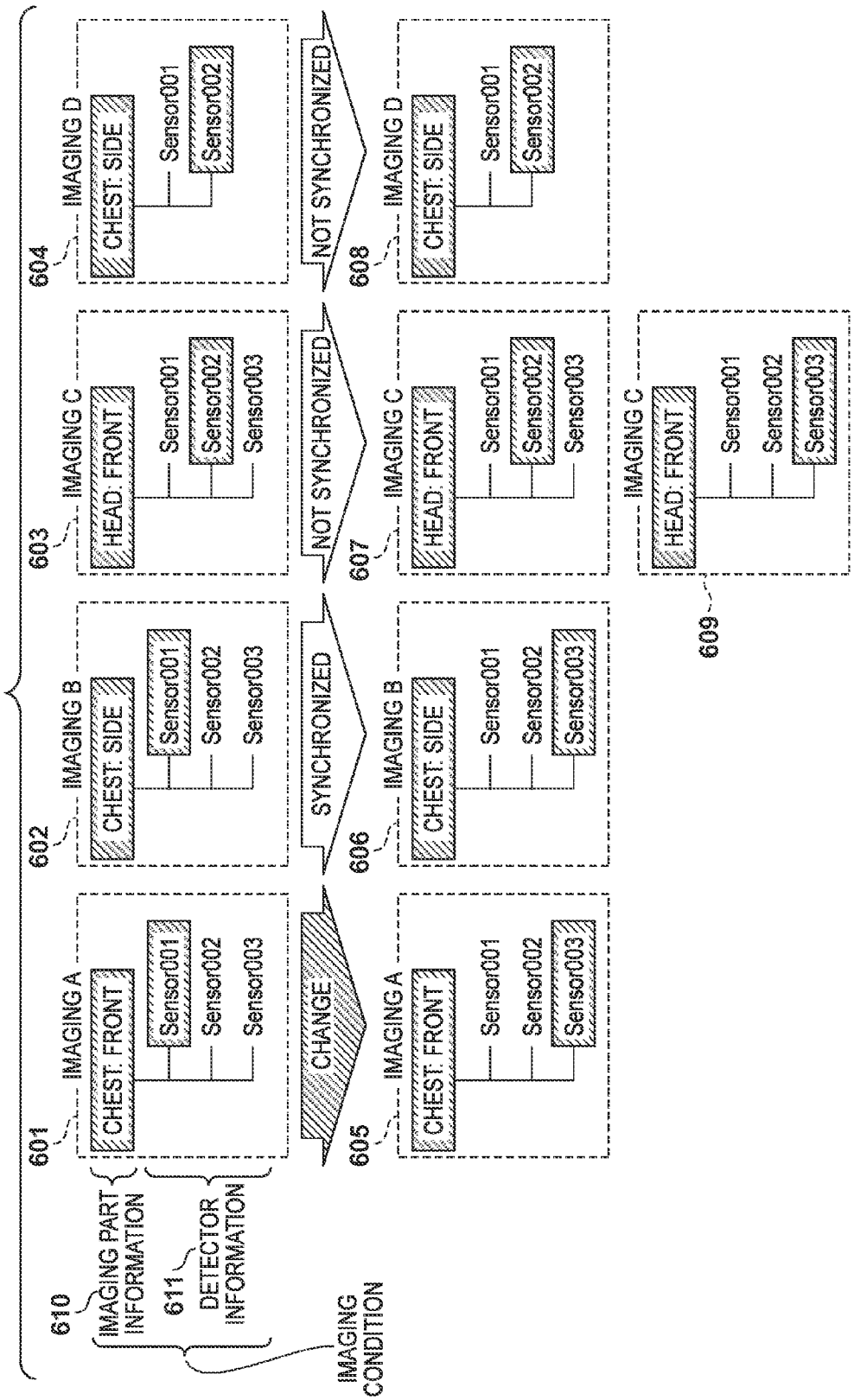

X-RAY IMAGING APPARATUS AND CONTROL METHOD

BACKGROUND OF THE INVENTION

Field of the Invention

The present invention relates to an X-ray imaging apparatus and a control method which facilitate changing an imaging condition.

Description of the Related Art

It is sometimes necessary to correct examination information for imaging performed by an X-ray imaging apparatus as in the following cases: when the examination information sent from an RIS (Radiology Information System) lacks information required by the X-ray imaging apparatus or has an error; and when it is not possible to use the examination information received from the RIS without any change because of specification differences. For this reason, there has been proposed, in Japanese Patent Laid-Open Nos. 2001-275988 and 2003-248723 (to be referred to as patent literatures 1 and 2 hereinafter), a method of correcting examination information or adding information to it before transmission to an X-ray imaging apparatus by installing a patient/examination information input terminal between an RIS and the X-ray imaging apparatus.

In addition, when executing an X-ray examination, it is sometimes difficult to execute the examination in accordance with designated examination content depending on the state of an X-ray detector or the condition of an examination target patient. In such a case, the operator needs to correct the detector to be used for the examination and posture information. In this case, it is difficult for the operator to know an X-ray detector suitable for a change, and hence he/she may perform a change to an inappropriate X-ray detector (for example, a wireless X-ray detector with a small battery charge). In consideration of such a problem, Japanese Patent Laid-Open No. 2012-050620 (to be referred to as patent literature 3 hereinafter) has proposed a method of presenting a wireless X-ray detector suitable for an examination among a plurality of wireless X-ray detectors. There has also been disclosed a method of easily perform a change to a usable detector in a hospital including both a CR (Computed Radiography) and an FPD (Flat Panel Detector) when changing the detector to be used for imaging from the CR to the FPD or the other way around (see Japanese Patent Laid-Open No. 2012-100797 (to be referred to as patent literature 4 hereinafter)).

However, the method disclosed in patent literatures 1 and 2 is designed to correct examination information before transmission to the X-ray imaging apparatus, and hence cannot cope with a case in which the X-ray imaging apparatus needs to correct the examination information. For example, patent literatures 1 and 2 give no consideration to how to cope with a case in which the condition of a patient or the state of an X-ray detector differs from that assumed at the stage of execution of imaging on the X-ray imaging apparatus side. In addition, although the method disclosed in patent literatures 3 and 4 facilitates discriminating examination information to be corrected, it is necessary to perform change processing for each of all imaging conditions within an examination. As described above, patent literatures 1 to 4 give no consideration to a case in which it is necessary to change an imaging condition such as the X-ray detector or radiographic imaging table to be used for imaging after examination content is confirmed on the imaging apparatus side, for example, after examination information is received from an RIS or the like.

SUMMARY OF THE INVENTION

An embodiment of the present invention provides an X-ray imaging apparatus and a control method which further facilitate a change in an imaging condition in examination information including a plurality of imaging techniques.

According to one aspect of the present invention, there is provided a control apparatus for an X-ray imaging system, the control apparatus comprising: an obtaining unit configured to obtain examination information including a plurality of imaging techniques and a plurality of imaging conditions corresponding to the plurality of imaging techniques; a changing unit configured to change content of a condition item of an imaging condition selected from the plurality of imaging conditions in accordance with an operation input from an operator; and an applying unit configured to apply a change made by the changing unit to an imaging condition other than the selected imaging condition of the plurality of imaging conditions.

Also, according to another aspect of the present invention, there is provided a control method for a control apparatus for X-ray imaging, the method comprising: an obtaining step of obtaining examination information including a plurality of imaging techniques and a plurality of imaging conditions corresponding to the plurality of imaging techniques; a changing step of changing content of a condition item of an imaging condition selected from the plurality of imaging conditions in accordance with an operation input from an operator; and an applying step of applying a change made in the changing step to an imaging condition other than the selected imaging condition of the plurality of imaging conditions.

Further features of the present invention will become apparent from the following description of exemplary embodiments (with reference to the attached drawings).

BRIEF DESCRIPTION OF THE DRAWINGS

FIG. 6 is a view showing an example of the data structure of imaging conditions according to the second embodiment;

DESCRIPTION OF THE EMBODIMENTS

The preferred embodiments of the present invention will be described below with reference to the accompanying drawings. Note that the following embodiments do not limit the invention according to the scope of claims, and not all the combinations of the features described in the embodiments are essential to the solving means of the invention.

First Embodiment

Figure 1:
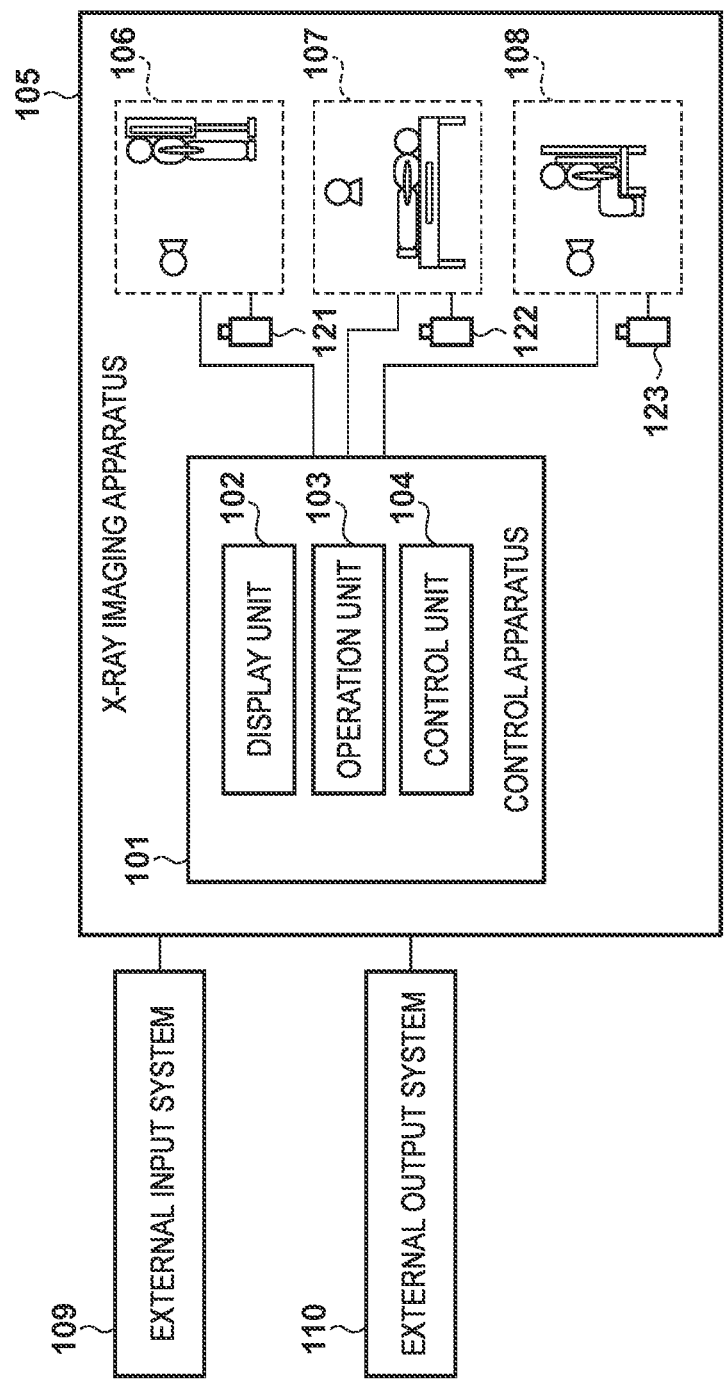
FIG. 1 is a block diagram showing the arrangement of a medical system according to the first embodiment.

FIG. 1 is a block diagram showing an example of the arrangement of a medical network system according to the first embodiment. Referring to FIG. 1, an X-ray imaging apparatus 105 can execute an X-ray examination based on the examination information input from an external input system 109. The external input system 109 is a system for inputting examination information to a control apparatus 101, and is implemented as, for example, an RIS. In addition, the operator may input examination information from an operation unit 103. A display unit 102 includes, for example, a liquid crystal display, and displays image data, GUI (Graphical User Interface), or the like on a screen. The operation unit 103 includes a mouse, a keyboard, and an irradiation switch, and accepts an instruction from the operator.

A control unit 104 has a function of performing imaging by controlling imaging units 106 to 108 and a function of performing image processing for obtained image data. The control unit 104 is configured to make a computer execute programs stored in, for example, memories (ROM and RAM) (not shown), and executes various types of processing (to be described later). The control apparatus 101 executes imaging upon switching the imaging unit to be used in accordance with imaging conditions associated with the plurality of imaging units 106 to 108 and included in examination information. Each of the imaging units 106 to 108 includes an X-ray generator and an X-ray detector, executes X-ray imaging under the imaging condition instructed from the control apparatus 101 in response to pressing of a corresponding one of exposure buttons 121 to 123 respectively provided for the imaging units 106 to 108, and transfers an obtained image to the control apparatus 101.

When the operator inputs information necessary for an examination and a command and issues an X-ray imaging instruction via the operation unit 103, the control unit 104 displays the obtained image received from the X-ray detector on the display unit 102. For example, the operator can also issue instructions to start and end an examination by the control apparatus 101 and an instruction to adjust a received image and edit examination information such as an imaging operator name and a patient name via the operation unit 103. The examination information of an executed examination and the obtained images included in the examination are transferred to an external output system 110 in response to an instruction from the operator. The external output system 110 is a system for saving and displaying the image transferred from the X-ray imaging apparatus 105, and is implemented as, for example, a PACS (Picture Archiving and Communication System).

Figure 2:
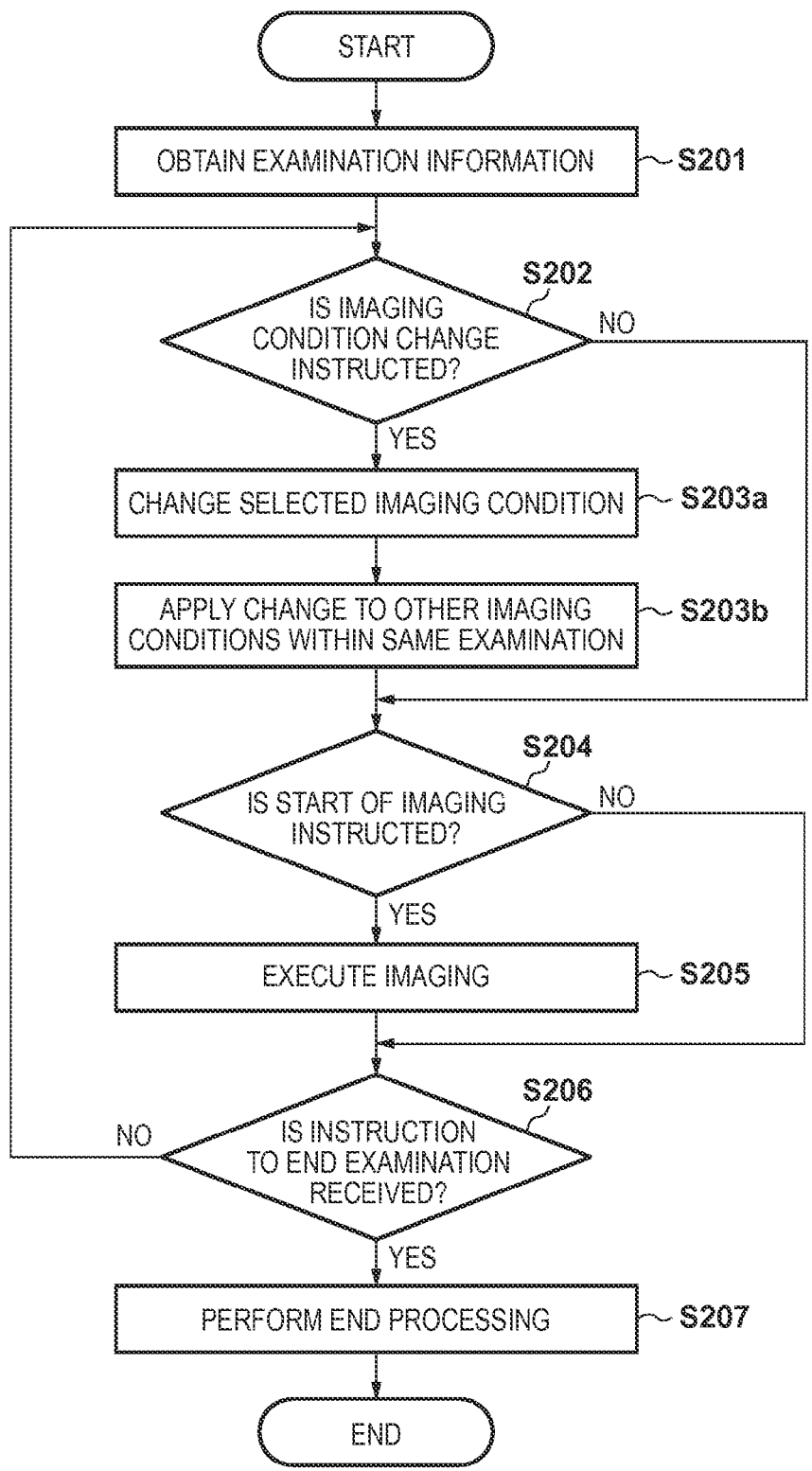
FIG. 2 is a flowchart showing switching synchronization processing for an imaging condition according to the first embodiment.

A basic procedure from the start of an examination to the end of the examination on an imaging screen will be described next with reference to the flowchart of FIG. 2.

First of all, at the start of an examination, the control apparatus 101 obtains examination information from the external input system 109 (step S201). Note that the examination information to be obtained may be the examination information input by the operator via the operation unit 103. The examination information includes a plurality of imaging techniques and a plurality of imaging conditions corresponding to these imaging techniques. The display unit 102 displays the imaging techniques and imaging conditions included in the examination information (to be described later with reference to FIG. 3). This display allows the operator of the control apparatus 101 to confirm the examination information (imaging condition) obtained in step S201 and confirm whether it is possible to execute the imaging technique indicated by the examination information. A situation in which a given imaging technique cannot be executed is, for example, a case in which the battery of the X-ray detector linked to received examination information has run out or a case in which a patient associated with "standing posture" as an imaging condition has come on a wheelchair to an examination room.

The operator can designate an imaging condition to be changed via the operation unit 103 and issue an instruction to change the content of a condition item included in the imaging condition. That is, upon receiving an operation input including an imaging condition change instruction indicating the selection of an imaging condition and the change of the content of a condition item from the operation unit 103 (step S202), the control unit 104 advances the process to step S203a. In accordance with the imaging condition change instruction, the control unit 104 changes the content of the condition item of the selected imaging condition (step S203a). The control unit 104 then applies the change made in step S203a to imaging conditions other than the selected imaging condition among the plurality of imaging conditions included in the examination information obtained in step S201 (step S203b). In this manner, the control unit 104 reflects the change of the imaging condition instructed from the operation unit 103 in the designated imaging condition, and also reflects the change in other imaging conditions of the imaging conditions included in the examination information obtained in step S201. The content of the imaging condition to be changed includes, for example, the change of the radiographic imaging table or X-ray detector to be used or the replacement of an imaging technique. In addition, according to this embodiment, in step S203b, the control unit 104 reflects the change in other imaging conditions, of the imaging conditions included in the examination conditions, which have not been used for imaging. Reflecting the change in the imaging condition which has not been used for imaging can properly reflect the change in imaging conditions even while the imaging technique indicated by the examination information is in progress. As described above, when one designated imaging condition is changed, the content of the change is reflected in all imaging conditions which have not been used for imaging within the same examination.

In this manner, the operator changes the imaging condition, which is included in the examination information and has not been used for imaging, to an imaging condition which can be executed, and executes imaging. That is, if the operator selects an imaging condition which has not been used for imaging from the imaging condition included in the examination conditions and issues an instruction to start imaging (step S204), X-ray imaging is executed under the set imaging condition (that is, by using the radiographic imaging table and the X-ray detector designated by the imaging condition) (step S205). Upon completing necessary X-ray imaging, the operator issues an instruction to end the examination via the operation unit 103 (for example, operates an end button 309 (FIG. 3)). Upon receiving the instruction to end the examination (step S206), the control unit 104 ends the display of the imaging screen on the display unit 102 or executes end processing such as outputting examination information to the external output system 110 (step S207), and ends the examination. On the other hand, if no examination end instruction is issued, the process returns to step S202. If, therefore, it is necessary to change an imaging condition during an examination, it is possible to change an imaging condition as in the above manner.

Figure 3:
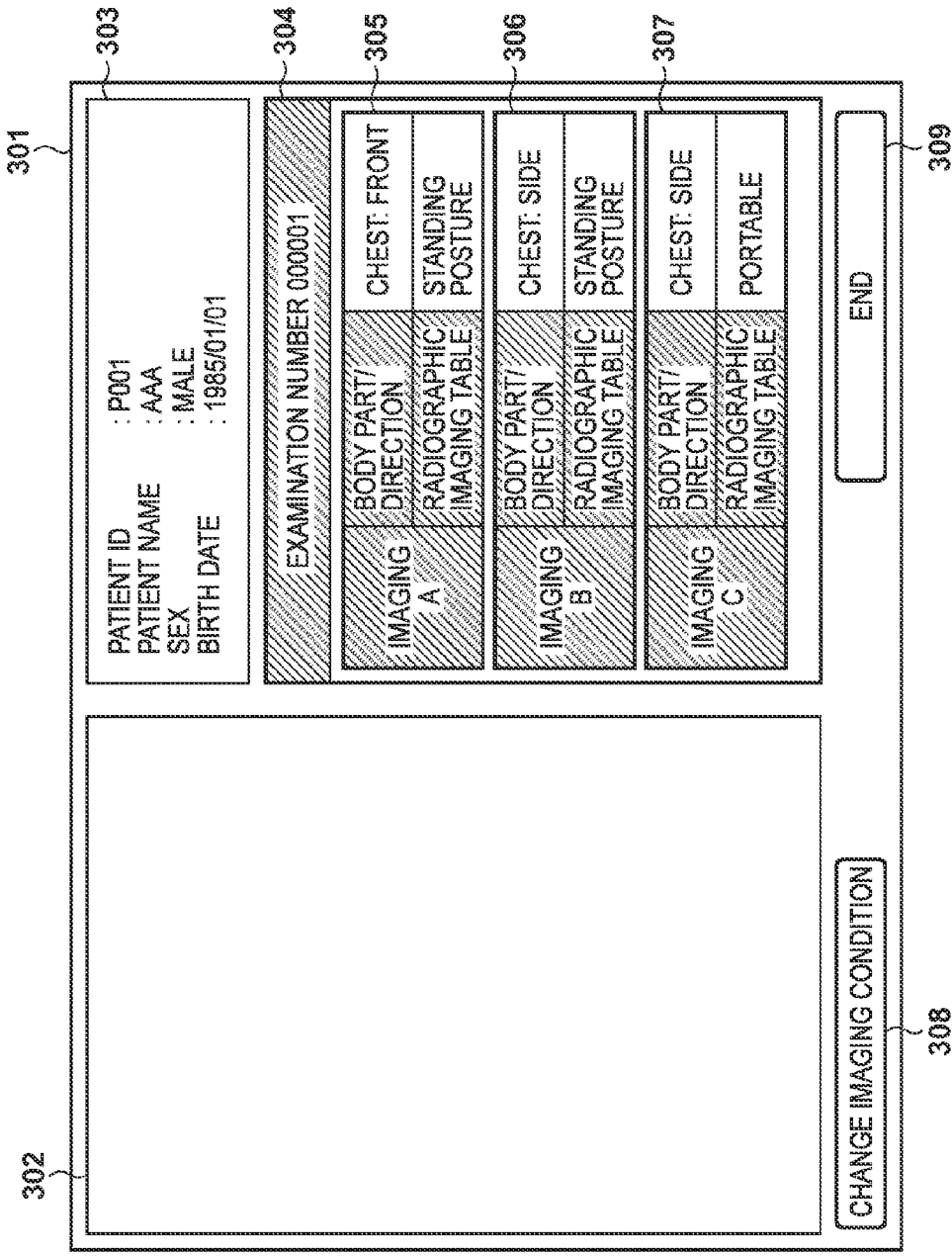
FIG. 3 is a view showing an example of an imaging screen according to the first embodiment.

An example of the operation of changing an imaging condition by the X-ray imaging apparatus according to the first embodiment will be described next with reference to FIGS. 3 to 5. FIG. 3 shows an example of a GUI on the display unit 102. An image display portion 302 which displays the image obtained from the X-ray imaging apparatus or database and a patient information display portion 303 which displays patient information corresponding to an example during display are provided on a display window 301. An examination information display portion 304 which displays an examination number, examination information, and the like is provided on the display window 301. In the case shown in FIG. 3, examination information with an examination number 000001 is obtained, which includes three imaging techniques, namely imaging A 305, imaging B 306, and imaging C 307. The display portion 304 shows imaging A 305, imaging B 306, and imaging C 307 executed in the examination. Note that this examination information includes three imaging conditions (to be described later with reference to FIG. 4) corresponding to the three imaging techniques.

When the operator selects desired imaging from the examination information display portion 304, and presses a corresponding one of the exposure buttons 121 to 123 for a corresponding one of the imaging units 106 to 108, the selected imaging is executed. Note that imaging execution buttons may be provided on the screen in FIG. 3 to allow the operator to execute imaging by using a selected imaging unit by pressing (for example, clicking) one of the buttons to issue an instruction. Alternatively, imaging execution permission buttons may be provided on the screen in FIG. 3. When the operator presses one of the buttons to issue an instruction, the execution of imaging may be permitted by pressing of the exposure button of the corresponding imaging unit. By detecting the transfer of an obtained image by the imaging unit, the control apparatus 101 can determine that the imaging technique has been "used for imaging". In addition, when the operator presses an imaging condition change button 308 during an examination, a changing screen 501 corresponding to the selected imaging is displayed (FIG. 5). FIG. 5 shows an example of a changing screen when the imaging condition change button 308 is pressed while imaging A is selected. Note that the changing screen 501 may be displayed when the operator operates, for example, double-clicks imaging A 305, imaging B 306, or imaging C 307 on the GUI. When the operator presses the end button 309, the examination is terminated.

Figure 4:
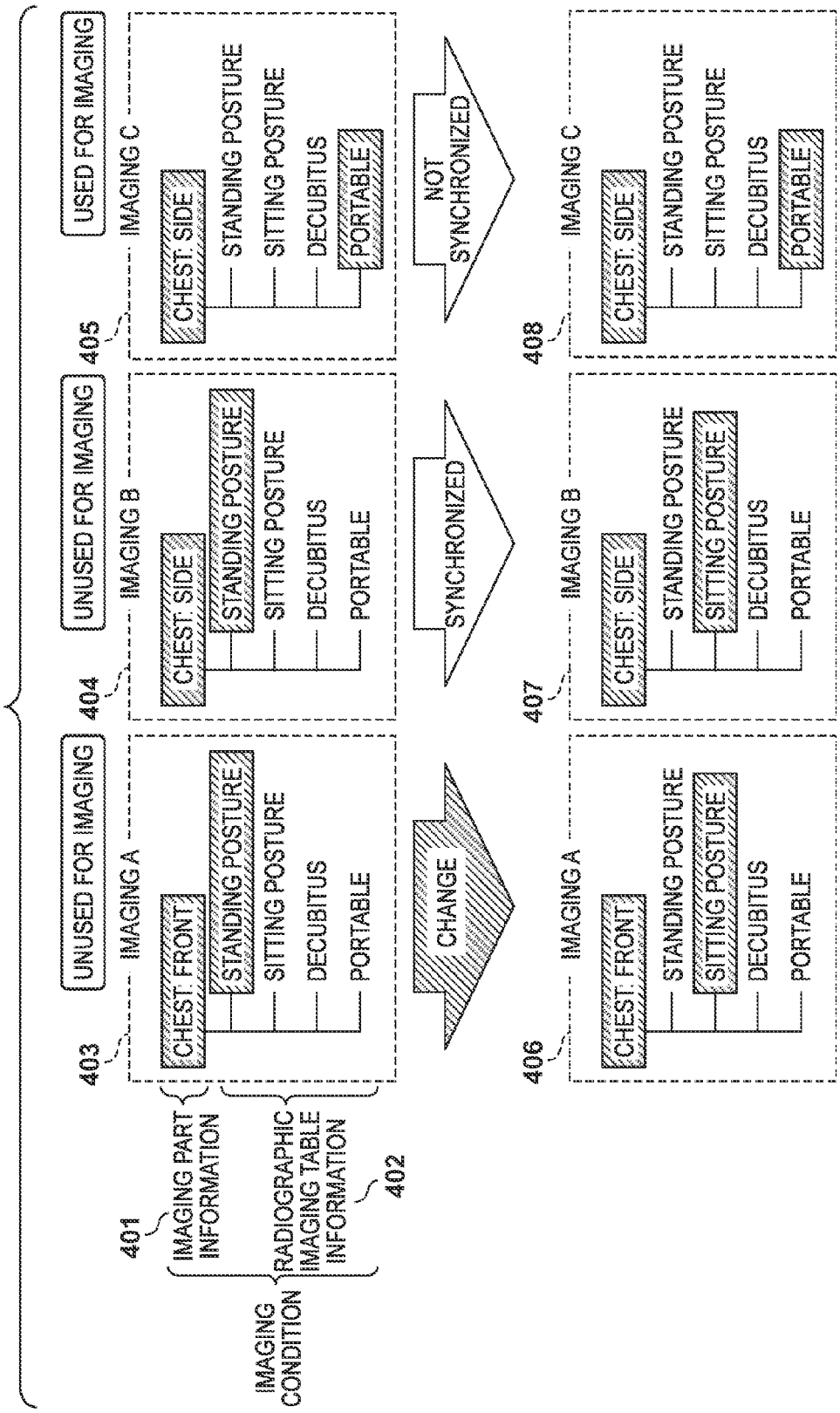
FIG. 4 is a view showing an example of the data structure of imaging conditions according to the first embodiment.
Figure 5:
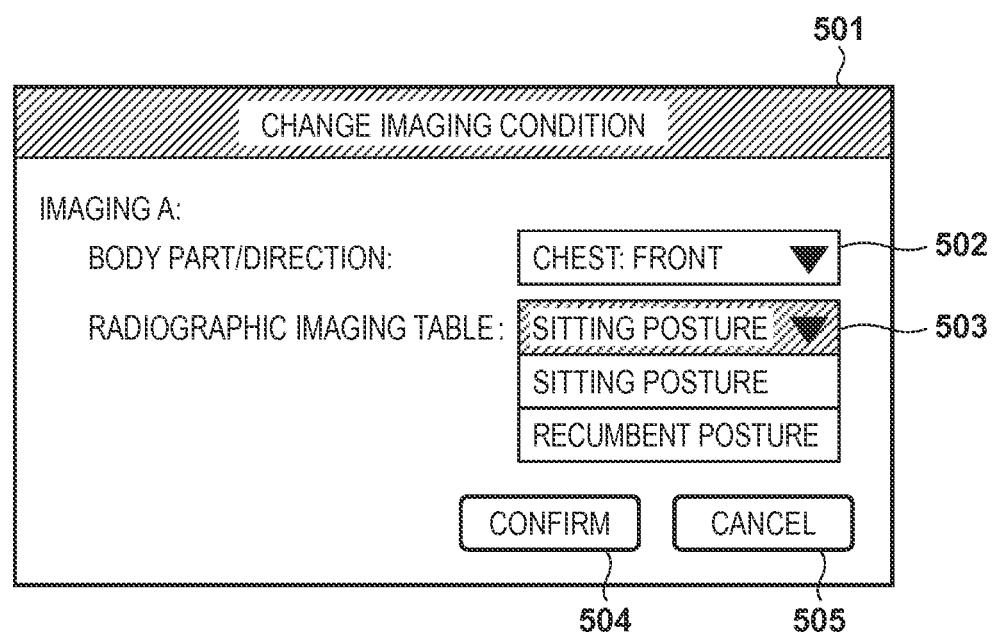
FIG. 5 is a view showing an example of a screen for changing an imaging condition according to the first embodiment.

FIG. 4 is a view showing the data arrangement of imaging conditions. Each imaging condition exemplarily shown in FIG. 4 includes two condition items, namely, imaging part information 401 including an imaging target part (body part) and an imaging direction and radiographic imaging table information 402 indicating the radiographic imaging table to be used. Referring to FIG. 4, imaging C 307 has been used for imaging. That is, FIG. 4 shows a case in which when a condition item of the imaging condition for imaging A 305 is changed after the execution of imaging C 307, the change is applied to other imaging conditions. Imaging conditions for the respective imaging techniques before the change of the imaging condition for imaging A 305 are an imaging condition 403 (imaging A 305), an imaging condition 404 (imaging B 306), and an imaging condition 405 (imaging C 307). When the operator selects imaging A 305 and operates the imaging condition change button 308 or double-clicks imaging A 305 on the display window 301, the control unit 104 causes the display unit 102 to display the changing screen 501 shown in FIG. 5. The operator can change the imaging condition for imaging A 305 by using the changing screen 501.

The changing screen 501 includes a part changing portion 502 and a radiographic imaging table changing portion 503. The operator can change imaging part information to an arbitrary imaging part/imaging direction by operating the part changing portion 502. The radiographic imaging table changing portion 503 displays a list of radiographic imaging tables which can be used for imaging using the imaging part information designated by the part changing portion 502. Upon executing an arbitrary imaging condition change, the operator confirms the operation by pressing a confirmation button 504. When the operator presses a cancel button 505, the imaging condition change is canceled. Assume that the operator has changed the imaging condition 403 for imaging A 305 from "standing posture" to "sitting posture" by operating the radiographic imaging table changing portion 503, as indicated by an imaging condition 406. In this case, the same radiographic imaging table information is applied to the imaging condition 404 for imaging B 306 to change the imaging condition to an imaging condition 407. In addition, since imaging C 307 has been performed, the synchronization of the radiographic imaging table information is not applied to the corresponding imaging information, and hence no change occurs in the imaging condition, as indicated by an imaging condition 408.

When the operator has changed imaging part information by operating the part changing portion 502, a change occurs in the imaging condition corresponding to the replacement of an imaging technique. In addition, referring to FIG. 4, the data structure of radiographic imaging table information 402 indicates the currently selected radiographic imaging table of selectable radiographic imaging table choices ("standing posture", "sitting posture", "decubitus", and "portable"). However, this is not exhaustive. For example, the radiographic imaging table information 402 may have a form in which a selected radiographic imaging table is simply written. In addition, all the imaging conditions shown in FIG. 4 include, as the radiographic imaging table information 402, the same choices ("standing posture", "sitting posture", "decubitus", and "portable"). However, this is not exhaustive. For example, while imaging A 305 has the four choices, namely "standing posture", "sitting posture", "decubitus", and "portable", the radiographic imaging table information 402 for imaging B 306 may have two choices, namely "standing posture" and "decubitus". In this case, even if the radiographic imaging table information 402 is changed to "sitting posture" in imaging A 305, the change of imaging A 305 cannot be reflected in imaging B 306 because this choice does not exist in imaging B 306. Such an operation will be described in the second embodiment. In addition, the first embodiment has exemplified a radiographic imaging table (radiographic imaging table information) as a condition item to be changed. However, this is not exhaustive. For example, an X-ray detector (detector information) may be set as a change target as exemplified by the second embodiment (FIG. 6).

Second Embodiment

In the application of a change to another imaging condition, which is performed in step S203b in the first embodiment, (to be also referred to as imaging condition switching synchronization hereinafter), when reflecting the content of the change to one imaging condition in another imaging condition, it is confirmed whether another imaging condition has not been used for imaging. According to the second embodiment, in switching synchronization of an imaging condition, a condition (synchronization condition) is provided to determine whether to perform synchronization (whether to apply the change) based on the content of a condition item of the imaging condition at the synchronization destination. That is, when applying the change executed with respect to the selected imaging condition in step S203a to a plurality of imaging conditions in step S203b, the change is applied to each imaging condition having the same content as that of a predetermined condition item of the condition items included in a selected imaging condition. The following will describe a case in which an imaging target part (imaging part) in an imaging technique is used as such a predetermined condition item, and a synchronization condition is that an imaging condition should include the same imaging part.

FIG. 6 is a view showing an example of the data arrangement of imaging conditions according to the second embodiment. Each imaging condition includes imaging part information 610 including an imaging target part and an imaging direction and detector information 611 indicating the X-ray detector to be used. Assume that an imaging condition 601 for imaging A, of imaging techniques, namely imaging A, imaging B, imaging C, and imaging D, included in examination information has been changed to an imaging condition 605 (Sensor001 of the detector information 611 is changed to Sensor003). In this case, an imaging condition 602 for imaging B includes the same imaging target (chest part) as that of the imaging condition 601 for imaging A, and hence satisfies a synchronization condition for imaging condition switching (including the same imaging part). For this reason, the detector information of the imaging condition 602 for imaging B is switched in synchronization with the switching of the detector information performed with respect to the imaging condition 601 for imaging A. As a result, the imaging condition 602 for imaging B is changed to an imaging condition 606. However, the imaging target of an imaging condition 603 for imaging C is "head part", which differs from the imaging part of the imaging condition 601 for imaging A. Therefore, the imaging condition 603 does not satisfy a synchronization condition, and hence the detector information is not switched. As a result, the imaging condition 603 for imaging B becomes an imaging condition 607, with its content being maintained.

In addition, imaging condition 604 for imaging D includes the same imaging target, and hence satisfies the synchronization condition for imaging condition switching. However, since the detector information 611 does not include the detector information (Sensor003) to which the detector information should be changed, the application of the change is inhibited. As a result, the imaging condition 604 for imaging D is not changed either, and the imaging condition 604 becomes an imaging condition 608. As described above, each of a plurality of imaging conditions included in examination information has a changeable range (the types of detectors which can be changed in this case) of a condition item (the detector information 611 in this case) included in each imaging condition. A control unit 104 inhibits the application of the change to an imaging condition to which the change to be applied falls outside the changeable range.

Figure 7A:
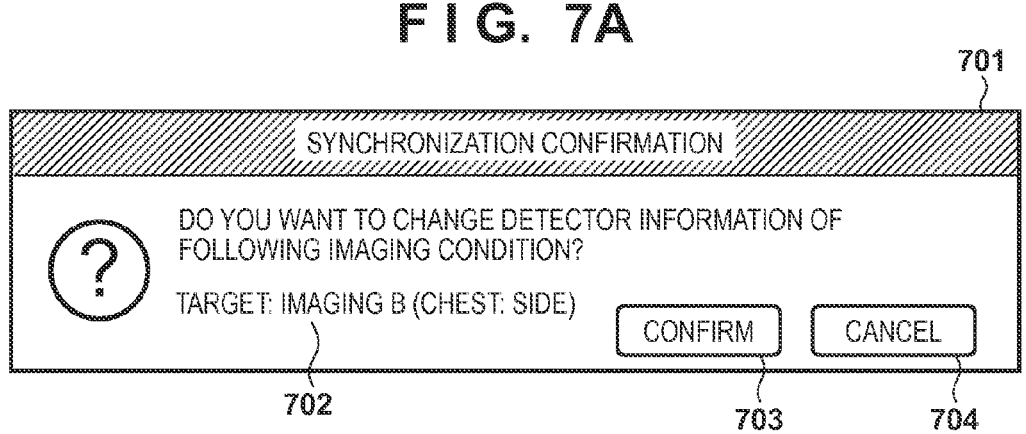
FIGS. 7A and 7B are views each showing an example of a confirmation window according to the second and eighth embodiments.

Note that with regard to an unchanged imaging condition, to which the application of change is inhibited because the change to be applied falls outside the changeable range, the operator may confirm whether to apply the change. For example, in step S203b, after an imaging condition change, a synchronization confirmation window 701 shown in FIG. 7A may be displayed on a display unit 102 to prompt the operator to designate whether to execute synchronization of an imaging condition which does not satisfy the switching synchronization condition. Although the synchronization confirmation window 701 in FIG. 7A displays the text "Do you want to change the detector information of the following imaging condition?", the word "detector information" is changed in accordance with the condition item to which a change is to be applied. If, for example, the condition item to which a change is to be applied is radiographic imaging table information, the synchronization confirmation window 701 displays the text "Do you want to change the radiographic imaging table information of the following imaging condition?".

A synchronization candidate display portion 702 displays an imaging condition candidate (imaging C in this case) which does not satisfy the imaging condition switching synchronization condition. When the operator presses a confirmation button 703, imaging condition switching synchronization is executed with respect to the imaging condition, displayed on the synchronization candidate display portion 702, which has not been used for imaging. With this operation, imaging change synchronization is executed with respect to the imaging condition 608 for imaging C to which the change has not been applied because the synchronization condition is not satisfied. As a result, the imaging condition is updated to an imaging condition 609. Note that if the operator does not execute imaging condition switching synchronization by the synchronization confirmation window 701, he/she presses a cancel button 704. When the operator presses the cancel button 704, the control unit 104 applies the change to only imaging conditions which satisfy the synchronization condition but does not apply the change to other imaging conditions. When the operator presses the confirmation button 703 or the cancel button 704, the display on the synchronization confirmation window 701 ends. Note that if there are a plurality of imaging conditions as targets to be confirmed by the synchronization confirmation window 701, the imaging conditions are displayed on the synchronization confirmation window 701. In this case, the operator may decide to synchronize or not synchronize a plurality of imaging conditions collectively or may individually make setting to synchronize or not synchronize with respect to a plurality of imaging conditions by using, for example, check boxes.

The above embodiment has exemplified the condition "including the same imaging target part" as an imaging condition switching synchronization condition. Obviously, however, this is not exhaustive. For example, it is possible to use the condition "including the same posture (standing posture, sitting posture, decubitus, or the like)" and the condition "an X-ray detector being a moving-image-compatible X-ray detector" as synchronization conditions. In addition, although the above embodiment has exemplified the change of detector information, it is obvious that the embodiment can be applied to the change of radiographic imaging table information as described in the first embodiment. Furthermore, the operator may be permitted to set a synchronization condition for imaging condition switching or make setting to validate/invalidate the use of a condition.

Third Embodiment

The first and second embodiments have exemplified the arrangement configured to change part of an imaging condition, that is, each condition item. The third embodiment will exemplify an arrangement configured to replace an imaging technique (overall imaging condition) included in examination information or confirm or cancel imaging condition switching synchronization.

Figure 8:
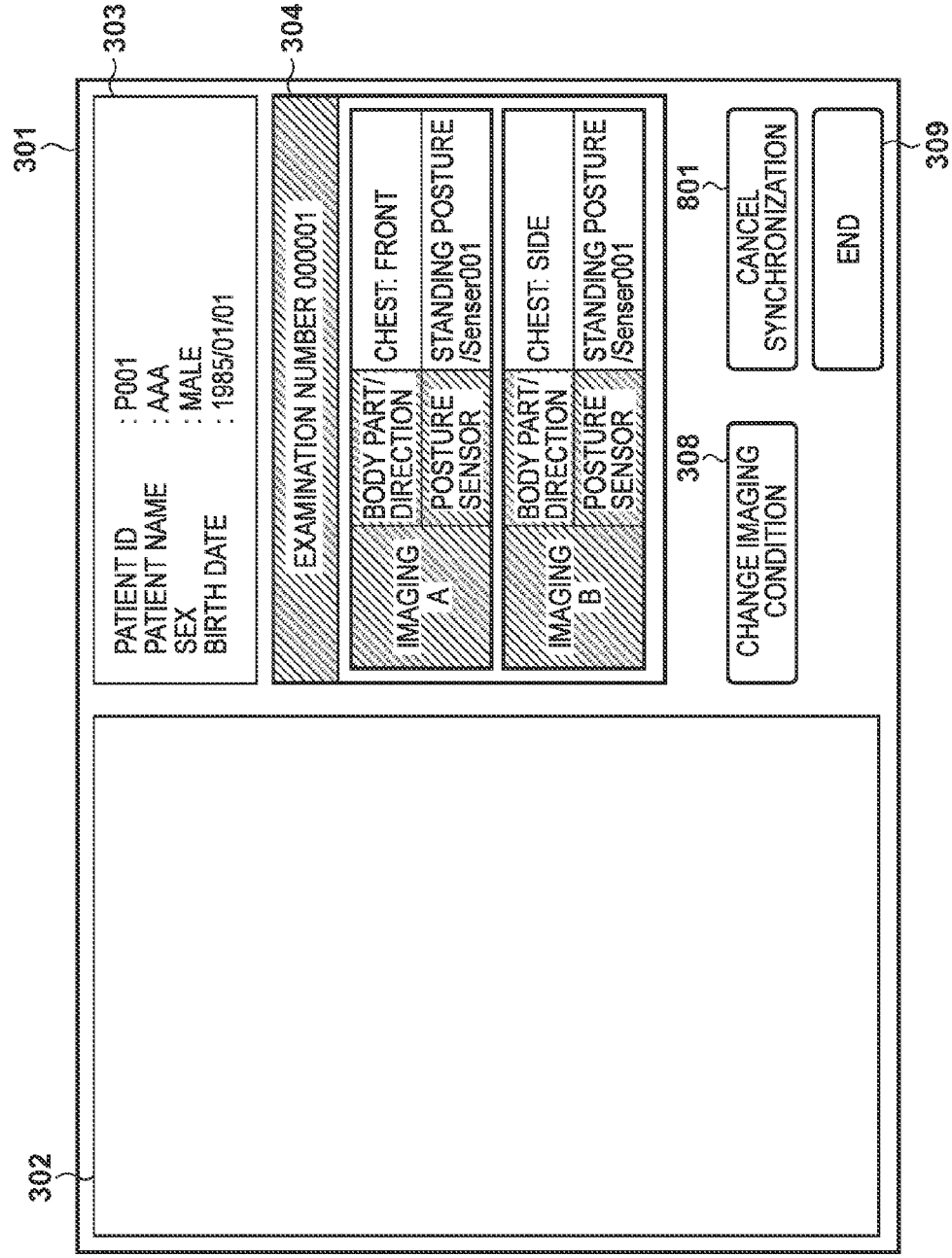
FIG. 8 is a view showing an example of an imaging screen according to the third embodiment.
Figure 9:
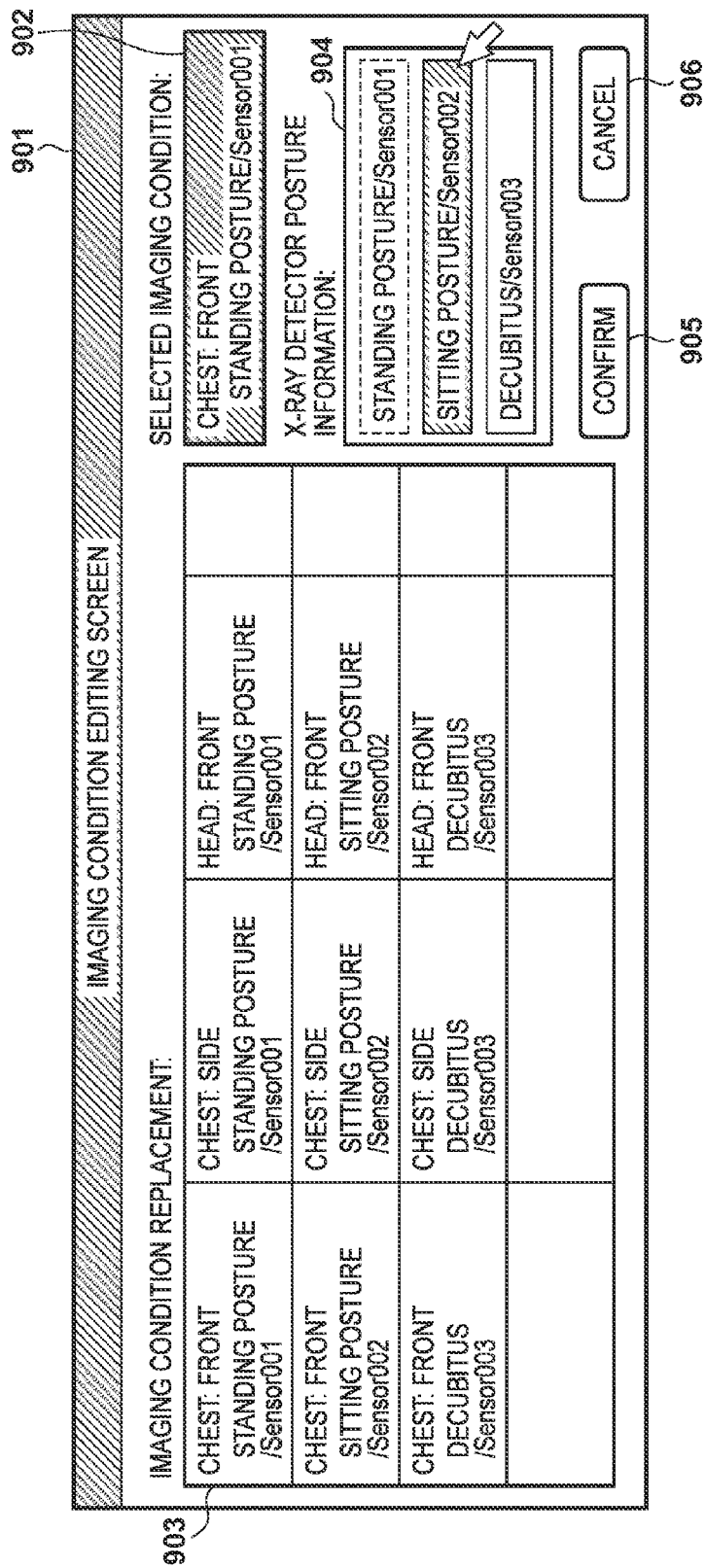
FIG. 9 is a view showing an example of a screen for changing an imaging condition according to the third embodiment.

FIG. 8 is a view showing an example of a GUI on a display unit 102 according to the third embodiment. According to the third embodiment, a display window 301 is provided with a synchronization cancel button 801 for canceling a synchronization change. When the operator presses an imaging condition change button 308, an editing screen 901 shown in FIG. 9 is displayed. Although the first embodiment has exemplified a changing screen 501 (FIG. 5) for a change of part of an imaging condition (change of a condition item), it is possible to replace an imaging technique to be executed on the editing screen 901. The editing screen 901 has an imaging condition display portion 902 which displays a selected imaging condition as an editing target, a replacement candidate display portion 903 which indicates a candidate which allows the replacement of an imaging condition, and a change candidate display portion 904 indicating changeable radiographic imaging table candidates. The editing screen 901 has a confirmation button 905 which confirms editing and a cancel button 906 which cancels editing.

The operator can replace an imaging condition by selecting another imaging condition from the replacement candidate display portion 903 or change radiographic imaging table information (detector information) of an imaging condition from the change candidate display portion 904. A confirmation instruction is issued by pressing the confirmation button 905 to execute confirmation processing. The result is reflected in examination information. In addition, a confirmation instruction may be issued by selecting change content on the replacement candidate display portion 903 or the change candidate display portion 904 or double-clicking on a GUI. When the operator presses the cancel button 906, all changes on the editing screen 901 are canceled, and the display on the editing screen 901 ends.

Furthermore, assume that an imaging condition switching synchronization condition presented in the second embodiment is applied. In this case, when radiographic imaging table information is changed from the change candidate display portion 904, imaging condition switching synchronization is executed based on a selected imaging condition displayed on the imaging condition display portion 902. Likewise, when a change is made by selecting another imaging condition from the replacement candidate display portion 903, that is, an imaging condition is replaced, other imaging conditions in the same examination information may be updated based on the imaging condition after the replacement. In this case, condition items of other imaging conditions which satisfy a synchronization condition concerning the imaging condition after the replacement may be changed to the content of the condition item of the imaging condition after the replacement. That is, an imaging condition matching a predetermined condition item of the condition items included in the imaging condition after the replacement may be updated. For example, as exemplified by the second embodiment, if a synchronization condition is "including the same imaging part", for example, radiographic imaging table information of other imaging conditions each including the same imaging part as that of the imaging condition after the replacement is changed to the radiographic imaging table information of the imaging condition after the replacement.

Note that when the confirmation button 905 is pressed on the editing screen 901, a synchronization confirmation window 701 for confirming whether to execute imaging condition switching synchronization with respect to other imaging conditions may be displayed. When the operator presses a confirmation button 703 on the synchronization confirmation window 701, imaging condition switching synchronization is executed with respect to imaging conditions which have not been used for imaging and satisfy the condition. When the operator presses a cancel button 704, the change is applied to only the imaging condition as an editing target displayed on the imaging condition display portion 902 but is not applied to the imaging condition displayed on a synchronization candidate display portion 702. When the operator presses a synchronization cancel button 801 after the end of the display of the synchronization confirmation window 701, the control unit 104 cancels the change of the imaging condition by imaging condition switching synchronization. When the operator presses the synchronization cancel button 801 while the change is canceled in this manner, the control unit 104 returns the examination information to the state before pressing of the imaging condition change button 308.

Fourth Embodiment

The first to third embodiments have exemplified imaging condition switching synchronization of radiographic imaging table information, detector information, and the like in the X-ray imaging apparatus. In this case, a given FPD as a detector may be changed to another FPD, or a given detector may be changed to another detector using a different recording method. If it is possible to change to a detector using a different recording method, it is possible to efficiently use an X-ray detector even in an X-ray imaging apparatus including a plurality of types of X-ray detectors.

Assume that a mobile X-ray car handles both an FPD and a CR. In this case, if imaging cannot be performed because of the shortage of the battery power of the FPD, it is possible to change the detector information to the CR under the imaging condition in which imaging by the FPD is designated.

Fifth Embodiment

Figure 10:
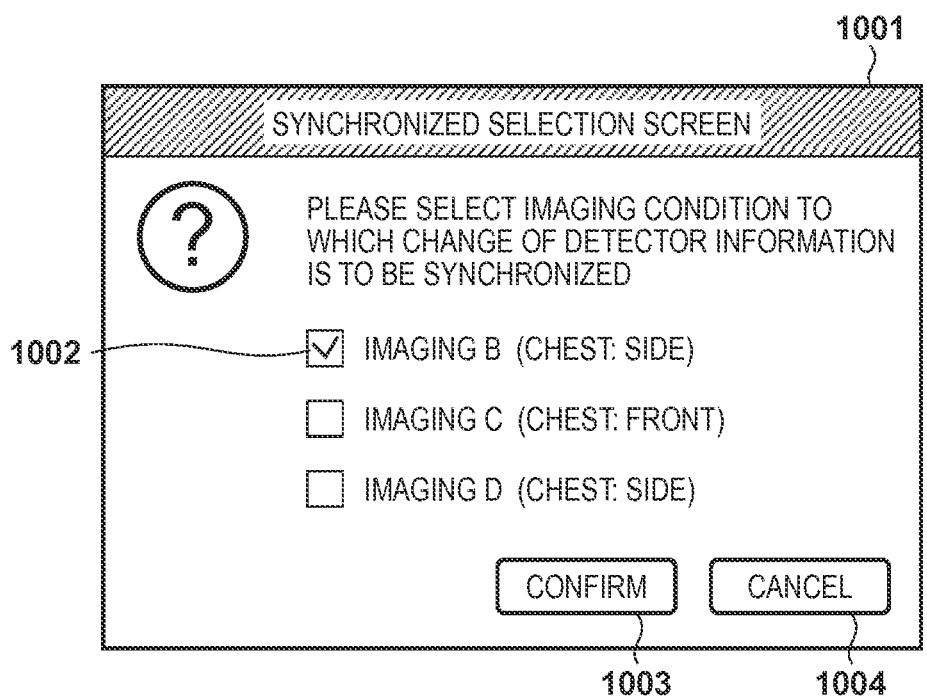
FIG. 10 is a view showing an example of a synchronized selection window according to the fifth embodiment.

The second and third embodiments have exemplified the case in which imaging condition switching synchronization is performed so as to synchronize all imaging conditions satisfying a condition. However, the present invention is not limited to this. For example, it is possible to make the operator arbitrarily select an imaging condition which permits imaging condition switching synchronization at the time of imaging condition switching. An arrangement configured to make the operator arbitrarily select an imaging condition which permits imaging condition switching synchronization will be described with reference to FIG. 10.

When an imaging condition change is executed, a synchronized selection window 1001 is displayed. A synchronization candidate display portion 1002 displays imaging condition candidates, of the imaging conditions included in examination information, to which imaging condition switching synchronization can be applied. When the operator selects an imaging condition to which imaging condition switching synchronization is to be executed from the synchronization candidate display portion 1002 and presses a confirmation button 1003, imaging condition switching synchronization is executed to the imaging condition selected on the synchronization candidate display portion 1002. When the operator presses a cancel button 1004, imaging condition switching synchronization is not executed regardless of the state of the synchronization candidate display portion 1002. When the operator presses the confirmation button 1003 or the cancel button 1004, the display of the synchronized selection window 1001 ends. Note that in the display of the text "Please select an imaging condition to which the change of detector information is to be synchronized" on the synchronized selection window 1001, the word "detector information" is changed in accordance with the condition item to which a change is to be applied as in the case of the synchronization confirmation window in FIG. 7A.

Sixth Embodiment

The first to third embodiments have exemplified the case in which imaging condition switching synchronization is performed so as to synchronize radiographic imaging table information and detector information. However, the present invention is not limited to the above embodiments, and synchronization may be executed with respect to other imaging conditions. For example, it is possible to synchronize only posture information of radiographic imaging table information or only X-ray detector information. Alternatively, it is possible to synchronize imaging part information or the like which is imaging technique information. The operator may be allowed to execute a setting operation for these pieces of information to be synchronized. That is, a change may be applied to a predetermined imaging condition included in imaging conditions. In addition, the operator may be allowed to set such a predetermined imaging condition.

Seventh Embodiment

Figure 11:
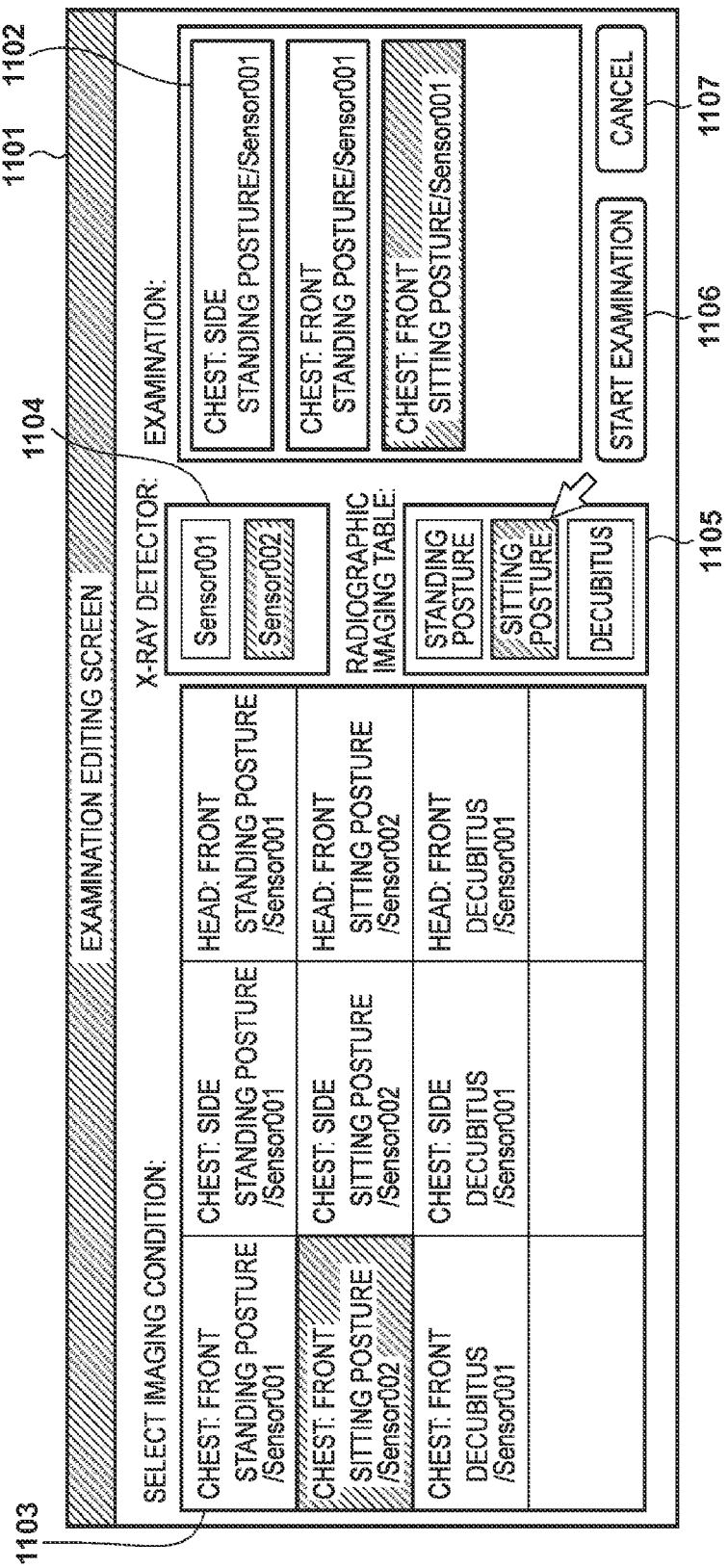
FIG. 11 is a view showing an example of an examination editing screen according to the seventh embodiment.

The first to sixth embodiments have exemplified the case in which imaging condition switching synchronization is executed on an imaging screen. However, an arrangement configured to perform imaging condition switching synchronization at the stage of generating examination information on an examination information setting screen will be described with reference to FIGS. 11 and 12.

A generating/editing screen 1101 (FIG. 11) is displayed when a control apparatus 101 generates and edits examination information without using an external input system 109 or when the examination information received from the external input system 109 is edited. A control unit 104 implements control associated with the generating/editing screen 1101 (to be described below).

An examination information display portion 1102 displays the imaging techniques (imaging conditions) included in examination information which is being generated or edited. The control unit 104 adds the imaging condition selected from a selection portion 1103 to the examination information and displays the resultant information on the examination information display portion 1102. In addition, the operator can set an X-ray detector or radiographic imaging table to be used in the selected imaging condition of the imaging conditions displayed on the examination information display portion 1102 from a detector setting portion 1104 or a radiographic imaging table setting portion 1105. Assume that sensor001 which is the portable FPD designated on the selection portion 1103 lacks battery power, and it is preferable to perform imaging by using sensor002 which is another portable FPD. In this case, sensor002 is selected from the detector setting portion 1104. This makes it possible to change the detector information of the imaging condition which is being generated or edited. In addition, if a patient planned to be imaged in a standing posture has come on a wheelchair to an imaging room, it is possible to change the radiographic imaging table information by selecting "sitting posture" from the radiographic imaging table setting portion 1105.

Figure 12:
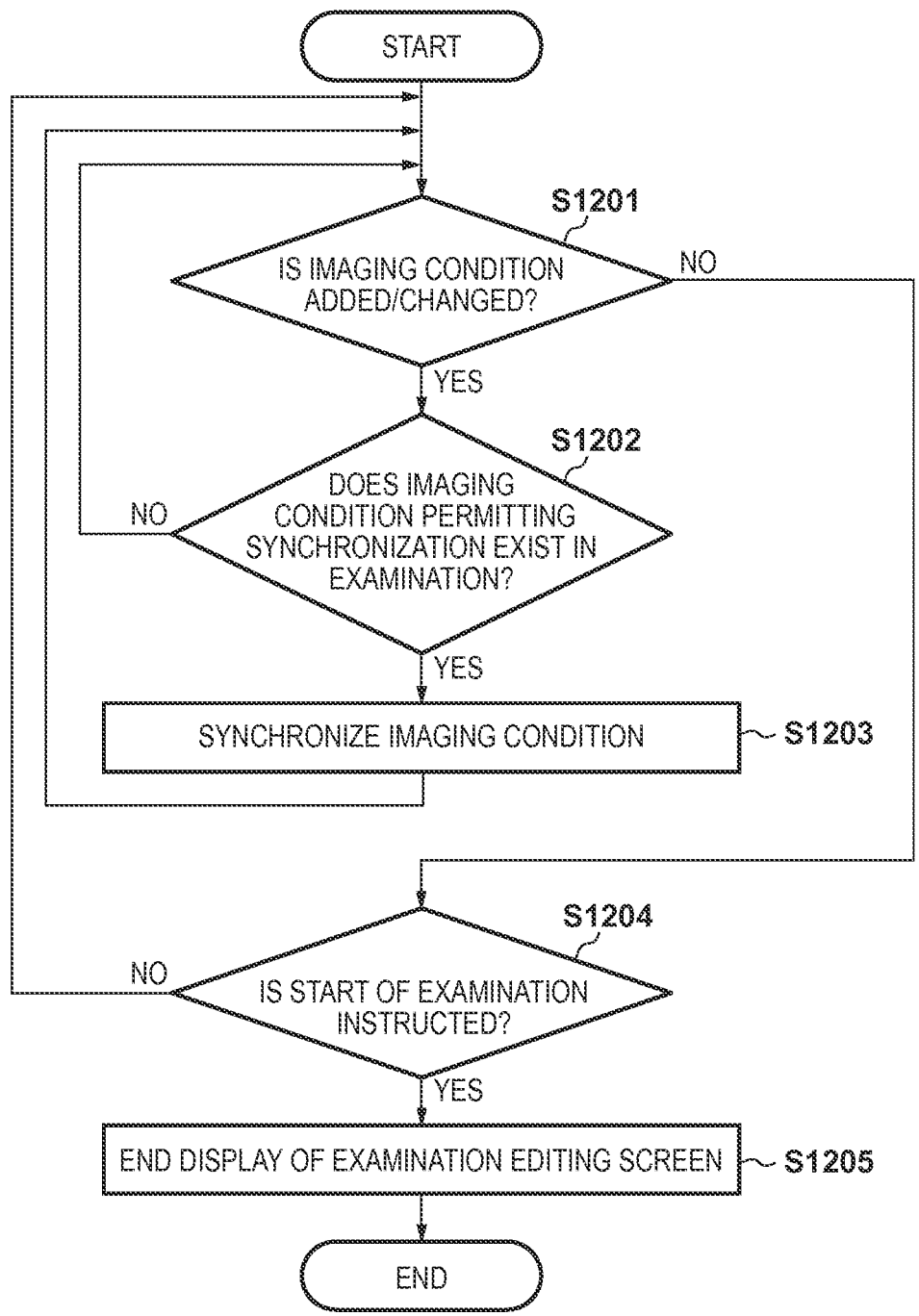
FIG. 12 is a flowchart showing switching synchronization processing for an imaging condition according to the seventh embodiment.

FIG. 12 is a flowchart for explaining the operation of the control unit 104 which controls the generating/editing screen 1101 described above. If a new imaging condition is added from the selection portion 1103 to an examination (step S1201), the control unit 104 determines based on the added imaging condition whether there is an imaging condition which satisfies an imaging condition switching synchronization condition (step S1202). The synchronization condition is the same as that described in the second embodiment. If there is an imaging condition satisfying the synchronization condition, the control unit 104 executes imaging condition switching synchronization (step S1203). Assume that when the synchronization condition is "including the same imaging part", an imaging condition that the front chest should be imaged in a sitting posture is added. In this case, with regard to added chest imaging, the imaging conditions are collectively changed synchronously so as to execute imaging by using the same radiographic imaging table as that designated by the added imaging condition. Likewise, when the operator selects added imaging and changes the imaging condition from the detector setting portion 1104 or the radiographic imaging table setting portion 1105, it is possible to collectively change the added imaging conditions synchronously. In this manner, the control unit 104 determines an imaging condition switching synchronization condition every time an imaging condition is added or changed. If an examination start 1106 or examination editing cancellation 1107 is instructed (step S1204), the display of the examination editing screen shown in FIG. 11 ends (step S1205).

Eighth Embodiment

Figure 7B:
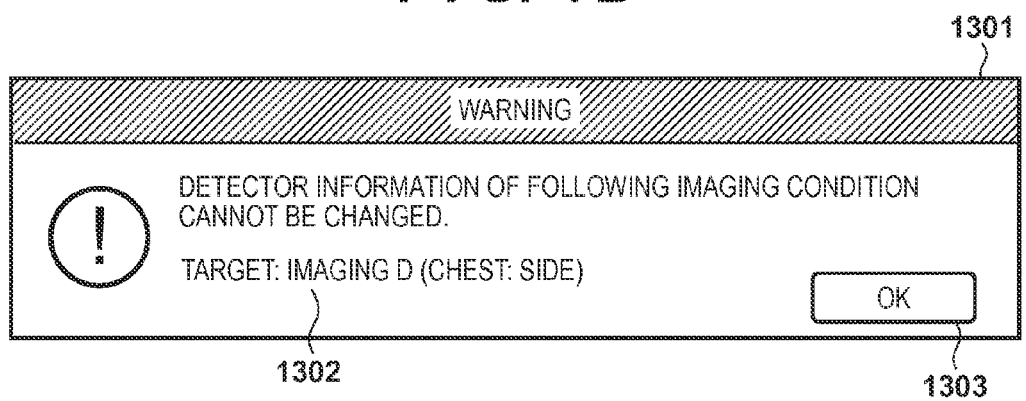

The second embodiment is configured to perform nothing for imaging which inhibits imaging condition switching synchronization. However, this is not exhaustive. According to the eighth embodiment, if there is an imaging condition which inhibits imaging condition switching synchronization because no detector or radiographic imaging table is linked even though a synchronization condition is satisfied or an imaging condition which inhibits synchronization of a change because a synchronization condition is not satisfied, this situation is called to attention by notification. If there is an imaging operation as a target for such calling of attention, a synchronization unexecutable warning window 1301 like that shown in FIG. 7B is displayed at the time of the execution of imaging condition switching synchronization. A display portion 1302 displays a list of imaging conditions which inhibit imaging condition switching synchronization. When the operator presses an OK button 1303, the non-synchronization warning window 1301 is closed.

As has been described above, each embodiment described above facilitates changing an imaging condition in examination information including a plurality of imaging techniques. If, for example, an imaging condition is changed due to a limitation imposed on an imaging method in accordance with the shortage of the battery power of a wireless X-ray detector or the condition of a patient, the content of the change is reflected in a plurality of imaging conditions included in the examination information. That is, based on editing performed on one of a plurality of imaging conditions by the operator, imaging conditions matching a synchronization condition within the same examination are collectively changed. It is therefore expected to reduce the number of operations performed by the operator, prevent operation errors, and shorten the examination time.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-073734, filed Mar. 31, 2014, which is hereby incorporated by reference herein in its entirety.

What is claimed is:

1. A control apparatus for an X-ray imaging system, the control apparatus comprising:
   an obtaining unit configured to obtain examination information including a plurality of imaging techniques and a plurality of imaging conditions corresponding to the plurality of imaging techniques;
   a changing unit configured to change content of a condition item of an imaging condition selected from the plurality of imaging conditions in accordance with an operation input from an operator, wherein the imaging condition includes, as the condition item, an imaging target part, an imaging posture and detector information indicating a detector to be used for X-ray imaging, and the changing unit changes at least one of the imaging target part, the imaging posture and the detector information; and
   an applying unit configured to apply a change made by said changing unit to an imaging condition other than the selected imaging condition of the plurality of imaging conditions.

2. The apparatus according to claim 1, wherein said applying unit applies the change to an imaging condition, of the plurality of imaging conditions, which has not been used for imaging.

3. The apparatus according to claim 1, wherein the change includes a change of a radiographic imaging table to be used for X-ray imaging.

4. The apparatus according to claim 1, wherein said applying unit applies the change to an imaging condition, of the plurality of imaging conditions, which includes content of a predetermined condition item, which matches content of the predetermined condition item of condition items included in the selected imaging condition.

5. The apparatus according to claim 4, wherein the predetermined condition item includes the imaging target part.

6. The apparatus according to claim 1, wherein each of the plurality of imaging conditions has a changeable range of a condition item included in each imaging condition, and
   said applying unit inhibits application of the change to an imaging condition to which the change to be applied falls outside the changeable range.

7. The apparatus according to claim 6, further comprising a confirming unit configured to make an operator confirm whether to apply the change to an unchanged imaging condition to which application of the change is inhibited, wherein
   said applying unit applies the change to the unchanged imaging condition when the operator applies the change.

8. The apparatus according to claim 6, further comprising a notifying unit configured to notify of existence of an imaging condition to which application of the change by said applying unit is inhibited.

9. The apparatus according to claim 1, further comprising a replacing unit configured to replace an imaging condition selected from the plurality of imaging conditions by an operator with another imaging condition.

10. The apparatus according to claim 9, further comprising an updating unit configured to update each imaging condition of the plurality of imaging conditions based on content of an imaging condition after replacement by said replacing unit.

11. The apparatus according to claim 10, wherein said updating unit updates an imaging condition, of the plurality of imaging conditions, which matches a predetermined condition item of conditions included in the imaging condition after the replacement.

12. The apparatus according to claim 1, wherein a change of the condition item includes selection of an X-ray detector which differs in a recording method.

13. The apparatus according to claim 1, further comprising a selecting unit configured to make an operator select an imaging condition which permits application of a change by said applying unit from the plurality of imaging conditions.

14. The apparatus according to claim 1, wherein said applying unit applies the change to the other imaging condition when content of a predetermined condition item included in an imaging condition is changed.

15. The apparatus according to claim 14, further comprising a setting unit configured to make an operator set the predetermined condition item.

16. The apparatus according to claim 1, further comprising a generating unit configured to generate the examination information in accordance with an operation input from an operator,
    wherein said changing unit and said applying unit function with respect to examination information which is being generated by said generating unit.

17. A control method for a control apparatus for X-ray imaging, the method comprising:
    obtaining examination information including a plurality of imaging techniques and a plurality of imaging conditions corresponding to the plurality of imaging techniques;
    changing content of a condition item of an imaging condition selected from the plurality of imaging conditions in accordance with an operation input from an operator, wherein the imaging condition includes, as the condition item, an imaging target part, an imaging posture and detector information indicating a detector to be used for X-ray imaging, and at least one of the imaging target part, the imaging posture and the detector information is changed in the changing; and
    applying a change made in the changing to an imaging condition other than the selected imaging condition of the plurality of imaging conditions.

18. A non-transitory computer readable storage medium storing a program for causing a computer to execute each step in a control method comprising:
    obtaining examination information including a plurality of imaging techniques and a plurality of imaging conditions corresponding to the plurality of imaging techniques;
    changing content of a condition item of an imaging condition selected from the plurality of imaging conditions in accordance with an operation input from an operator, wherein the imaging condition includes, as the condition item, an imaging target part, an imaging posture and detector information indicating a detector to be used for X-ray imaging, and at least one of the imaging target part, the imaging posture and the detector information is changed in the changing; and
    applying a change made in the changing to an imaging condition other than the selected imaging condition of the plurality of imaging conditions.

* * * * *